(12) United States Patent
Li et al.

(10) Patent No.: US 12,106,404 B2
(45) Date of Patent: Oct. 1, 2024

(54) LABEL-FREE ADAPTIVE CT SUPER-RESOLUTION RECONSTRUCTION METHOD, SYSTEM AND DEVICE BASED ON GENERATIVE NETWORK

(71) Applicant: ZHEJIANG LAB, Zhejiang (CN)

(72) Inventors: Jingsong Li, Hangzhou (CN); Yiwei Gao, Hangzhou (CN); Peijun Hu, Hangzhou (CN); Tianshu Zhou, Hangzhou (CN); Yu Tian, Hangzhou (CN)

(73) Assignee: ZHEJIANG LAB, Hangzhou (CN)

( * ) Notice: Subject to any disclaimer, the term of this patent is extended or adjusted under 35 U.S.C. 154(b) by 0 days.

(21) Appl. No.: 18/363,703

(22) Filed: Aug. 1, 2023

(65) Prior Publication Data
US 2024/0169610 A1 May 23, 2024

(30) Foreign Application Priority Data
Nov. 16, 2022 (CN) .......................... 202211435386.X

(51) Int. Cl.
*G06T 11/00* (2006.01)
*G06T 3/4053* (2024.01)
(Continued)

(52) U.S. Cl.
CPC .......... *G06T 11/006* (2013.01); *G06T 3/4053* (2013.01); *G06T 5/70* (2024.01);
(Continued)

(58) Field of Classification Search
None
See application file for complete search history.

(56) References Cited

U.S. PATENT DOCUMENTS

2019/0287654 A1* 9/2019 Curtis ................. G16B 20/00
2020/0111194 A1* 4/2020 Wang ................. G06N 3/047
(Continued)

FOREIGN PATENT DOCUMENTS

CN 114241077 A 3/2022
CN 114581304 A 6/2022

OTHER PUBLICATIONS

Y. Sui, O. Afacan, C. Jaimes, A. Gholipour and S. K. Warfield, "Scan-Specific Generative Neural Network for MRI Super-Resolution Reconstruction," in IEEE Transactions on Medical Imaging, vol. 41, No. 6, pp. 1383-1399, Jun. 2022, doi: 10.1109/TMI.2022.3142610.*

(Continued)

*Primary Examiner* — Jiangeng Sun
(74) *Attorney, Agent, or Firm* — W&G Law Group

(57) ABSTRACT

The present application discloses a label-free adaptive CT super-resolution reconstruction method, device and system based on a generative network, which comprises the following modules: an acquisition module configured for acquiring low-resolution original CT image data; a preprocessing module configured for performing super-resolution reconstruction on original CT images based on total variation to obtain an initial value; and a super-resolution reconstruction module configured for performing high-resolution reconstruction on the initial value. According to the present application, a parameter fine-tuning method is adopted, and a CT reconstruction network which is not suitable for a certain patient is adjusted into a network which is suitable for the patient's situation on the premise of not using a large number of data sets for training; only the low-resolution CT data of the patient is used in this process, and the corresponding high-resolution CT data is not needed as a label.

10 Claims, 2 Drawing Sheets

(51) Int. Cl.
*G06T 5/70* (2024.01)
*G16H 30/40* (2018.01)
(52) U.S. Cl.
CPC ........... *G06T 11/005* (2013.01); *G16H 30/40* (2018.01); *G06T 2207/10081* (2013.01); *G06T 2207/20081* (2013.01); *G06T 2207/20084* (2013.01); *G06T 2207/30004* (2013.01); *G06T 2207/30168* (2013.01); *G06T 2211/441* (2023.08)

(56) References Cited

U.S. PATENT DOCUMENTS

| | | | |
|---|---|---|---|
| 2021/0088605 A1* | 3/2021 | Shi | G01R 33/5608 |
| 2022/0335573 A1 | 10/2022 | Zhu et al. | |
| 2023/0058112 A1* | 2/2023 | Salomon | G06N 20/00 |
| 2023/0076809 A1* | 3/2023 | Chaudhary | A61B 6/5217 |
| 2023/0316462 A1* | 10/2023 | Goshen | G06T 5/20 |
| | | | 382/128 |

OTHER PUBLICATIONS

Notice Of Allowance(CN202211435386.X); Date of Mailing: Jan. 18, 2023.
Super-resolution-reconstruction-of-medical-images-using-feature-based-loss.
A-New-Kind-of-Super-Resolution-Reconstruction-Algorithm-Based-on-the-ICM-and-the-Bilinear-Interpolation.

* cited by examiner

LABEL-FREE ADAPTIVE CT SUPER-RESOLUTION RECONSTRUCTION METHOD, SYSTEM AND DEVICE BASED ON GENERATIVE NETWORK

CROSS-REFERENCE TO RELATED APPLICATIONS

The present application claims priority to Chinese Patent Application No. 202211435386.X, filed on Nov. 16, 2022, the content of which is incorporated herein by reference in its entirety.

TECHNICAL FIELD

The present application relates to the technical field of medical imaging, in particular to a label-free adaptive CT super-resolution reconstruction method, system and device based on a generative network.

BACKGROUND

Computed tomography (CT) imaging is one of the most popular medical imaging methods for screening, diagnosis and image-guided intervention therapy. On this basis, high-resolution CT images are conducive to improving the authenticity of radiological features and assisting medical diagnosis more accurately. Therefore, super-resolution reconstruction has gained extensive attention in the field of CT. The image resolution of a CT imaging system is limited by the size of X-ray focal, detector element spacing, reconstruction algorithm and other factors. Although the physiological and pathological unit in human body is about 10 microns, the in-plane and inter-plane resolution of the clinical CT system is about sub-millimeter or 1 millimeter. The modern CT imaging system and visualization software can generate arbitrarily small voxels, but the inherent resolution thereof is still far below the ideal resolution in important applications such as early tumor characterization and coronary artery analysis. Therefore, it is very necessary to generate high-resolution CT images at the minimum radiation dose level. The methods usually used to improve CT resolution focus on hardware and calculation. Using more complex hardware components with higher scanning accuracy can improve the imaging effect of CT, but it usually means expensive capital investment and has to make concessions on imaging speed and radiation dose. However, high radiation dose levels will lead to genetic damage and increase the risk of cancer diseases. Therefore, the second method of improving resolution based on calculation is more practical, that is, obtaining high-resolution CT images from low-resolution CT images, and does not cause additional harm to patients.

Super-resolution reconstruction technology based on deep learning is usually oriented to training data, not to specific patients, so a large number of paired images are needed for training, in which low-resolution images are used as input, and the corresponding high-resolution images are used as labels. However, in reality, it is difficult to obtain satisfactory image quality, and reinjection of high radiation dose to obtain high-resolution CT data will cause secondary harm to patients. In addition, the super-resolution reconstruction model usually contains a large number of parameters that need to be optimized during training. After the model training is completed, the up-sampling factor of super-resolution reconstruction is fixed. Because the image resolution may be different in different scanning environments or for different patients, it is impossible to apply the trained depth model to any low-resolution CT image to obtain the required high-resolution results. In addition, the image contrast of subjects from different groups may be very different. Therefore, even if there are enough high-resolution training data sets available, the current super-resolution reconstruction model for training data cannot guarantee that it can be applied to low-quality CT super-resolution reconstruction tasks for all patients after training. Although no system can be perfectly applied to all patients at present, a method can be invented to fine-tune the network specific to a certain patient without the paired data sets of low-resolution CT and high-resolution CT, and only use the low-resolution CT images of the patient to train the network, so that it can adapt to the requirements of special situations. The present application proposes a method and system for performing CT super-resolution reconstruction based on the technology of a generative network, which has the characteristics of using no paired data set and targeting specific patients. This method realizes high-quality super-resolution reconstruction by deep learning technology, and at the same time, it only needs to use the low-resolution CT of the patient to train the model, without the corresponding high-resolution CT, eliminating the dependence on the training data set, and then allowing the super-resolution reconstruction model to be customized for individual patients.

SUMMARY

The present application aims to provide a label-free adaptive CT super-resolution reconstruction method, system and device based on a generative network, so as to overcome the shortcomings in the prior art.

In order to achieve the above purpose, the present application provides the following technical solutions.

The present application provides a label-free adaptive CT super-resolution reconstruction method based on a generative network; the method includes the following steps:

S1, acquiring original CT image data, preprocessing the original CT image data by a super-resolution reconstruction algorithm based on total variation to obtain an image to be reconstructed, and combining the image with random noise and inputting combined data into the generative network to enhance the robustness of the generative network;

S2, the generative network reconstructing the preprocessed image by using a nonlinear generation function to obtain a high-resolution CT image, and inputting the high-resolution CT image into a degradation network;

S3, the degradation network processing the high-resolution CT image by rigid body transformation matrices, slice coding matrices and down-sampling matrices, and adding Gaussian noise to obtain a low-resolution CT image; and S4, the generative network and the degradation network jointly affecting a loss function, updating parameters of the generative network in a back propagation, while keeping the degradation network unchanged, which mainly comprises the following steps: comparing the low-resolution CT image obtained by the degradation network with the original data, and adding the low-resolution CT image into the loss function of the generative network by using a Euclidean norm as a constraint; calculating a total variation regularization term for the reconstructed high-resolution CT image; adding the total variation regularization term to the loss function by using a sparse rule operator as a constraint to improve the clarity of the high-resolution CT image and preserving details of edges of the image; calculating a gradient of loss function by using an Adam algorithm, and realizing update of the parameters of the generative network.

Preferably, the step of obtaining the image to be reconstructed in step S1 comprises the following sub-steps:

step S1.1, obtaining an initial high-resolution CT image from an original low-resolution CT image by a super-resolution reconstruction algorithm based on total variation, wherein the super-resolution reconstruction algorithm based on total variation comprises a geometric transformation matrix, a motion blur matrix and a sampling matrix;

step S1.2, obtaining gradient transformation of each CT slice in X and Y directions according to the initial high-resolution CT image and pixel coordinates thereof;

step S1.3, obtaining the total variation regularization term of the initial high-resolution CT image according to the gradient transformation of the initial high-resolution CT image in X and Y directions; and step S1.4, adding the above total variation regularization term to the loss function of the super-resolution reconstruction algorithm based on total variation, and continuously optimizing the loss function by a gradient descent method to obtain a minimum value thereof, and obtaining the image to be input into the generative network for reconstruction.

Preferably, in step S1, the random noise v obeys Gaussian distribution, each element is independently extracted from $v \sim N(0,\sigma^2)$; a size of the noise is controlled by a parameter σ; if Gaussian noise is not needed, σ=0.

Preferably, in step S2, the generative network is pre-trained on CT data of a same target area in advance, so as to speed up a convergence speed when fine-tuning parameters for specific patients, and to improve the reconstruction effect; N low-resolution original CT image data of individual patients are obtained and used to train the generative network to realize CT super-resolution reconstruction, which can realize a customized CT super-resolution reconstruction system for individual patients.

Preferably, in step S3, a value of a $k^{th}$ rigid body transformation matrix is calculated by aligning a $k^{th}$ low-resolution original CT image with a first original CT image.

Preferably, in step S3, a slice thickness $\Delta z_x$ of the reconstructed high-resolution CT image is smaller than a slice thickness $\Delta z_k$ of the obtained low-resolution CT image; when low-resolution CT images are obtained from a high-resolution CT image by the degradation network, each low-resolution CT image is operated corresponding to a plurality of CT slices of the high-resolution CT image; slice distribution of the high-resolution CT image in the z direction is selected by introducing a slice coding matrix, a Gaussian distribution with a wide base and a narrow central peak is selected to represent the slice coding matrix, and a full width at half maximum of the slice coding matrix is a $\Delta z_k/\Delta z_x$ voxel in z direction.

Preferably, in step S3, the down-sampling operation is performed in a frequency domain, and all high-frequency components are truncated by a low-pass filter before down-sampling in the frequency domain to avoid signal aliasing.

Preferably, in step S3, a signal-to-noise ratio of the reconstructed high-resolution CT image is calculated, and the noise in the high-resolution CT image is measured by a standard deviation between an image area and background; if the signal-to-noise ratio is greater than 3, the noise at this time is similar to a Gaussian distribution, and in a degradation process, noise complying with a same Gaussian distribution is added; if the signal-to-noise ratio is less than or equal to 3, no additional noise is added.

Preferably, in step S4, the total variation regularization term is added to the reconstructed high-resolution CT image, image gradients in three orthogonal directions of the reconstructed high-resolution CT image are calculated and constrained by sparse rule operators, and weight parameters are added to the total variation regularization term to be added to the loss function and used to train and update the parameters of a nonlinear generation function in the generative network together with a loss part of the degradation network in the loss function.

Preferably, in step S4, an iterative strategy of jointly optimizing the high-resolution CT image x reconstructed by the generative network and a parameter θ in the nonlinear generation function or a technique of alternately optimizing the high-resolution CT image x and the parameter θ in the nonlinear generation function is adopted to solve the problem of calculating a minimum value of the loss function.

The present application provides a label-free adaptive CT super-resolution reconstruction system based on a generative network; the system includes the following modules:

an acquisition module configured for acquiring low-resolution original CT image data;

a preprocessing module configured for performing super-resolution reconstruction on original CT images based on total variation to obtain an initial value; and a super-resolution reconstruction module configured for performing high-resolution reconstruction on the initial value, wherein the module comprises a generative network based on deep learning and a degradation network for fitting low-resolution images from high-resolution images; the generative network and the degradation network jointly affect a loss function, and update parameters of the generative network in a back propagation while the degradation network remains unchanged.

The present application provides a label-free adaptive CT super-resolution reconstruction device based on a generative network; the device includes a memory and one or more processors, wherein executable codes are stored in the memory, and when executing the executable codes, the one or more processors implements the above label-free adaptive CT super-resolution reconstruction method based on a generative network.

The present application has the following beneficial effects: according to the label-free adaptive CT super-resolution reconstruction method, the system and the device based on a generative network, a patient-specific network is constructed by a method using no paired data sets, and the super-resolution reconstruction of CT images is performed so as to obtain high-quality CT images from low-quality CT data, so that the images have higher resolution, thus facilitating the diagnosis of doctors, and better formulating the treatment solution of patients; according to the present application, a parameter fine-tuning method is adopted, and a CT reconstruction network which is not suitable for a certain patient is adjusted into a network which is suitable for the patient's situation on the premise of not using a large number of data sets for training, and only the low-resolution CT data of the patient is used in this process, and the corresponding high-resolution CT data is not needed as a label, so that the problem that the situation varies from person to person in medical data can be flexibly dealt with, and the method has excellent generalization; the technology of this present application aims to reconstruct an image with a higher spatial resolution than the actually obtained image, while ensuring a high signal-to-noise ratio.

DESCRIPTION OF EMBODIMENTS

Figure 1:
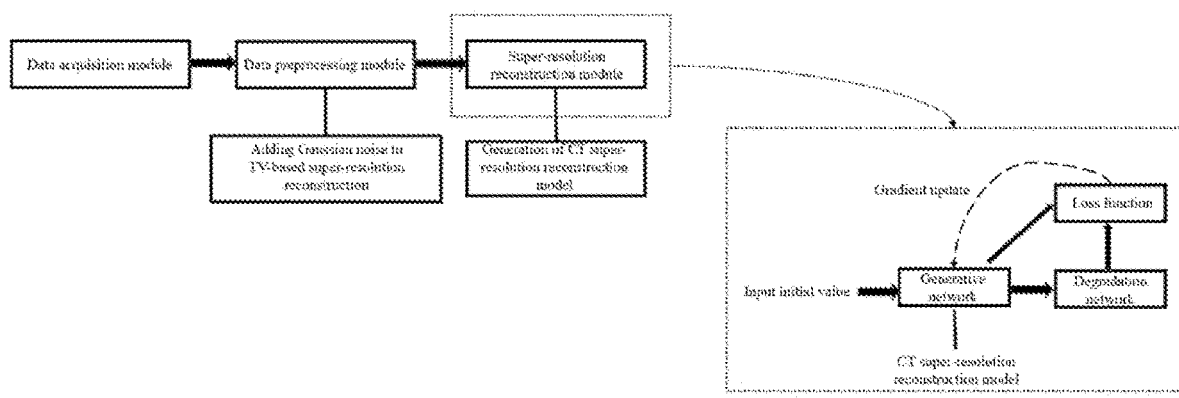
FIG. 1 is a system schematic diagram of an embodiment of the present application.

In order to make the purpose, technical solution and advantages of the present application more clear, the present application will be further explained in detail through the attached drawings and examples. However, it should be understood that the specific embodiments described herein are only for explaining the present application, and are not used to limit the scope of the present application. In addition, in the following description, descriptions of well-known structures and technologies are omitted to avoid unnecessarily confusing the concepts of the present application.

Because the general CT image reconstruction method based on data neural network needs a large number of paired data sets in the process of model training, it is difficult to obtain the data with one-to-one correspondence between high resolution and low resolution in CT images, and it cannot cover all the situations. The network trained in limited data sets usually has no good generalization. The purpose of the present application is to provide a CT reconstruction method and system based on generative network, which can train paired data sets specifically for patients, in view of the shortcomings of the above methods, such as difficulty in obtaining paired data sets and low generalization of networks.

In the embodiment of the present application, the following terms will be explained:

Total Variation (TV) regularization term: a sum of the square of the difference between each pixel in the image and the next pixel in the horizontal direction and the squares of the difference between the pixel and the next pixel in the vertical direction is solved, and then the square root is calculated; TV regularization is to smooth the image by gradient descent and smooth it inside, so that the difference between adjacent pixels is small and the outline of the image is not smoothed as much as possible.

Super-resolution reconstruction algorithm based on TV: the minimum TV is taken as the objective function, the gradient descent method is used to solve related problems, and the optimal solution of the objective function and the reconstructed high-resolution image are obtained.

An embodiment of the present application provides a label-free adaptive CT super-resolution reconstruction method based on a generative network, which includes the following steps:

In step S1, original CT image data are acquired, the original CT image data are preprocessed by a super-resolution reconstruction algorithm based on total variation to obtain an image to be reconstructed, and the image is combined with random noise and inputting combined data into the generative network to enhance the robustness of the generative network;

in step S1.1, an initial high-resolution CT image is obtained from an original low-resolution CT image by a super-resolution reconstruction algorithm based on total variation; the super-resolution reconstruction algorithm based on total variation comprises a geometric transformation matrix, a motion blur matrix and a sampling matrix;

in step S1.2, gradient transformation of each CT slice in x and y directions are obtained according to the initial high-resolution CT image and pixel coordinates thereof;

in step S1.3, the total variation regularization term of the initial high-resolution CT image is obtained according to the gradient transformation of the initial high-resolution CT image in x and y directions;

in step S1.4, the above total variation regularization term is added to the loss function of the super-resolution reconstruction algorithm based on total variation, and the loss function is continuously optimized by a gradient descent method to obtain a minimum value thereof, and the image to be input into the generative network for reconstruction is obtained.

In step S2, the generative network reconstructs the preprocessed image by using a nonlinear generation function to obtain a high-resolution CT image, and inputs the high-resolution CT image into a degradation network.

In step S3, the degradation network processes the high-resolution CT image by rigid body transformation matrices, slice coding matrices and down-sampling matrices, and adds Gaussian noise to obtain a low-resolution CT image.

In step S4, the generative network and the degradation network jointly affect a loss function, the parameters of the generative network are updated in a back propagation, while the degradation network remains unchanged, which mainly includes the following steps: comparing the low-resolution CT image obtained by the degradation network with the original data, and adding the low-resolution CT image into the loss function of the generative network by using a Euclidean norm as a constraint; calculating a total variation regularization term for the reconstructed high-resolution CT image, and adding the total variation regularization term to the loss function by using a sparse rule operator as a constraint to improve the clarity of the high-resolution CT image and preserve details of edges of the image; calculating a gradient of loss function by using an Adam algorithm, and realizing update of the parameters of the generative network.

Figure 2:
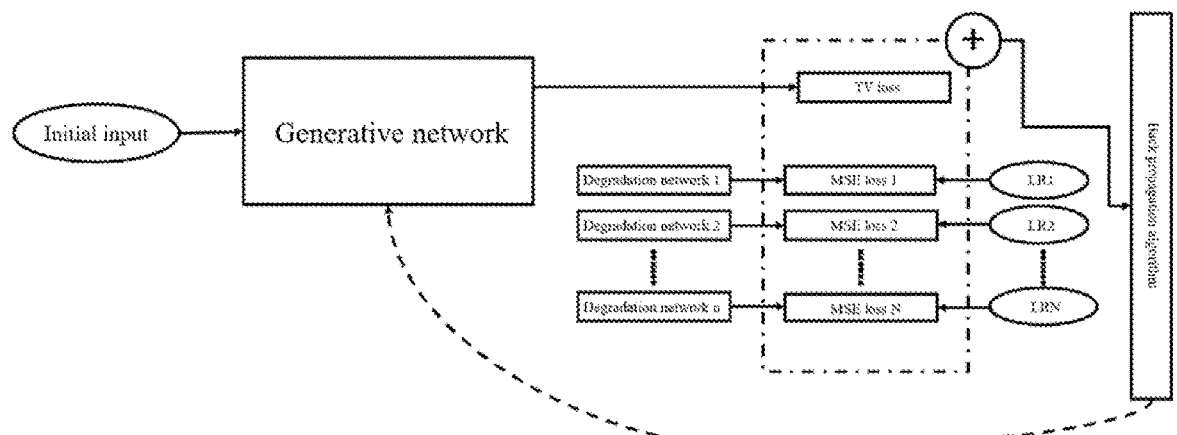
FIG. 2 is an architecture diagram of a super-resolution reconstruction module according to an embodiment of the present application.

As shown in FIG. 1, an embodiment of the present application also provides a label-free adaptive CT super-resolution reconstruction system based on a generative network, which includes an acquisition module for acquiring low-resolution CT image data; a preprocessing module for performing super-resolution reconstruction on the original CT image based on Total Variation (TV) to obtain an initial value; a super-resolution reconstruction module for high-resolution reconstruction of the initial value, which includes a generative network based on deep learning and a degradation network for fitting low-resolution images from high-resolution images. Both the generative network and the degradation network affect the loss function together, and the parameters of the generative network are updated in the back propagation, while the degradation network remains unchanged. The architecture of the super-resolution reconstruction module is shown in FIG. 2.

I. The specific execution steps of the data acquisition and preprocessing module are as follows:

1) CT scanning is performed on a target part of a patient to obtain original data o, where the o is a low-resolution CT image;

2) the original CT image o is reconstructed by a TV-based super-resolution reconstruction algorithm to get an initial value z, which is input into the generative network as the image to be reconstructed; the equation for obtaining z is:

$$\min \|z\|_{TV} \text{ s.t. } o = DHFz \quad \|z\|_{TV} = \|D_1 z\|_1 + \|D_2 z\|_1$$

$$D_1 = \sum_{i,j} |z_{i,j} - z_{i-1,j}| * z \quad D_2 = \sum_{i,j} |z_{i,j} - z_{i,j-1}| * z$$

where i and j represent the pixel coordinates in the original image z, $\|z\|_{TV}$ represents a TV regularization term of z, $D_1$ represents the gradient transformation in the z direction, $D_2$ represents the gradient transformation in the y direction, and $\|\cdot\|_1$ is a norm of $l_1$; o=DHFz is the imaging model of the TV-based super-resolution reconstruction algorithm, and F is the geometric transformation matrix; H is a motion blur matrix; D is the sampling matrix, o is the known low-resolution CT image, and z is the high-resolution CT image to be obtained; a gradient descent method is used to optimize the algorithm, and the specific solution objective is shown in the following formula:

$$\arg\min_o (\|z\|_{TV} + \frac{1}{2} \|DHF_z - o\|_2^2);$$

where $\|\cdot\|_2$ is a norm of $l_2$. The minimum value of the above formula is obtained through continuous optimization, and z at this time is input into the generative network as the result. From o to z, the resolution and signal-to-noise ratio of the image have been improved. At this time, the purpose of inputting z into the generative network is to reconstruct an image with higher resolution.

Figure 3:
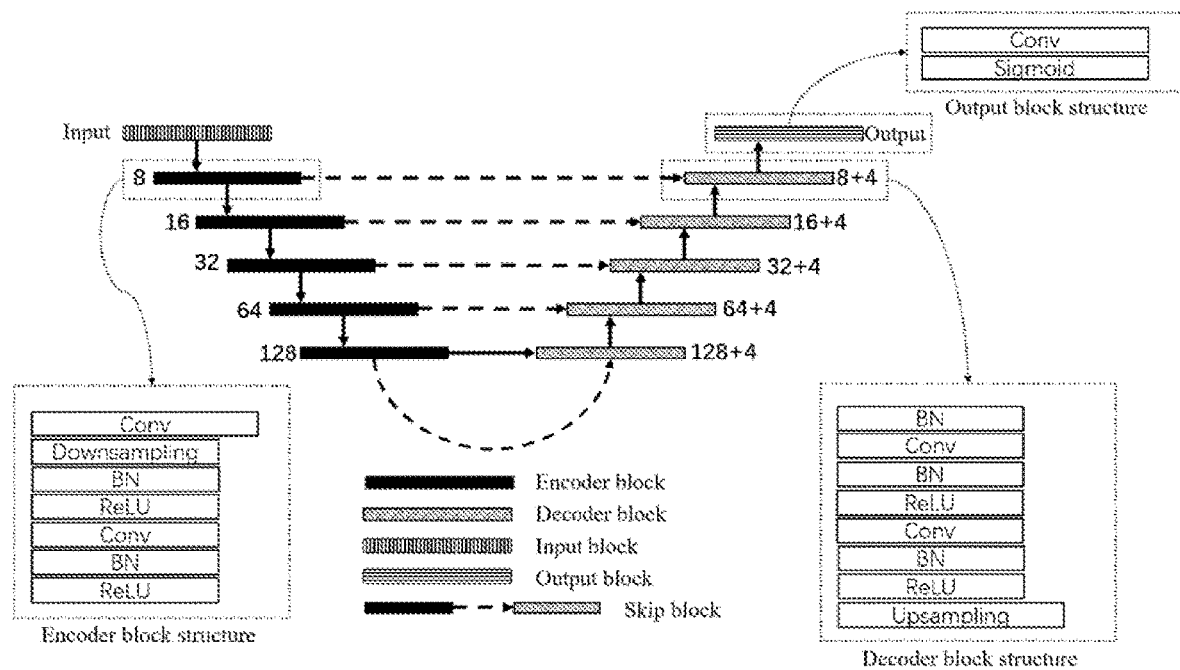
FIG. 3 is a schematic structural diagram of a generative network according to an embodiment of the present application.

II. The specific execution steps of the super-resolution reconstruction module are as follows:

1) in the process of generating a high-resolution CT image using a generative network based on deep neural learning, the image z obtained by the preprocessing module is input into the network, and a high-resolution CT image x is obtained after processing, and the process is expressed by the following formula:

$$x = f_\theta(Z);$$

where z represents the initial value of the input network; $f_\theta$ is a set of nonlinear generation functions based on z and defined by a parameter θ, which is realized by the generative network. The generative network in the present application can be pre-trained on the CT data of the same target area in advance, which is helpful to accelerate the convergence speed of fine-tuning parameters for specific patients and improve the reconstruction effect. Because $f_\theta$ is customized for individual patients, only N low-resolution CT data $\{o_k\}_{k=1}^N$ of specific patients can be used to train the generative network to characterize $f_\theta$. The structure of the generative network is shown in FIG. 3.

The generative network has a layer structure similar to 3D U-Net, which includes five encoder blocks, five decoder blocks, five skip blocks, an input block and an output block, and the number of channels generated by convolution in each block is displayed beside the block. Each skip block generates four additional channels, which are connected to the convolutional input channels in the corresponding decoder block. The convolution kernel size in each convolution layer of encoder and decoder blocks is 3×3×3 voxels, and the convolution kernel size in skip blocks is 1×1×1 voxels. All convolutions adopt reflection filling strategy. The extraction step of the Downsampling layer is 2×2×2 voxels, and the Upsampling layer adopts trilinear interpolation with a factor of 2. The output block consists of a convolution layer with a convolution kernel size of 1×1×1 voxel and a sigmoid layer with a standardized mesh output.

2) Assuming that the number of input data of the network is N, the high-resolution CT image reconstructed by the generative network is x, and the low-resolution CT image reconstructed by the degradation network is $y_k$, k=1, 2, ..., N, and a forward model describing the imaging of the degradation network can be expressed as:

$$y_k = D_k H_k T_k x + \varepsilon_k \quad k=1,2,\ldots,N$$

where, the matrix $T_k$ represents the rigid body transformation in the image coordinates; $H_k$ is the slice coding matrix for slice selection; $D_k$ stands for downsampling; $\varepsilon_k$ means adding noise. These matrices are described in detail below.

Rigid body transformation matrix $T_k$: since the patient may move during CT scanning, the position of the target organ in the CT sequence will be relatively offset. In order to make the degraded $y_k$ more close to the real situation during the degradation operation, the rigid body transformation $T_k$ is used to represent this motion, and it is applied to the reconstructed high resolution image x. The value of $T_k$ is calculated by aligning the $k^{th}$ low-resolution CT image with $o_k$ the first image $o_1$, and the relationship between them is $o_k = T_k o_1$, therefore, $T_k = o_k o_1^T$, where $o_1^T$ represents the transposition of $o_1$.

Slice coding matrix $H_k$: since the reconstructed high-resolution CT image x and the degraded low-resolution CT $y_k$ image have different slice thicknesses, $\Delta z_x$ represents the slice thickness of x, and $\Delta z_k$ represents the slice thickness of $y_k$. Generally, $\Delta z_k > \Delta z_x$, i.e., there are more CT slices in x. Therefore, in the process of obtaining $y_k$ through X degradation, each $y_k$ needs to be operated corresponding to multiple CT slices in X. At this time, a slice coding matrix $H_k$ is needed to select the slice distribution in z direction for x. $H_k$ is essentially a spatially invariant low-pass filter. An ideal slice distribution is a rectangular window function whose full width is related to the slice thickness. It needs a sinc pulse, which needs an infinite number of side lobes to uniformly excite discrete frequency bands, so it is practically impossible to generate a perfect rectangular profile. Therefore, in the present application, a Gaussian distribution with a wider base and a narrower central peak is used to represent $H_k$, and the Full Width at Half Maximum (FWHM) of $H_k$ is a $$\frac{\Delta z_k}{\Delta z_x}$$

voxel in the z direction. Since FWHM=$2\sqrt{2\ln 2}\sigma$ in Gaussian function, $H_k$ can be expressed by $$H_K \sim N(0, \frac{\Delta z_k}{8\ln 2 \Delta z_x}^2). \, N(0, \frac{\Delta z_k}{8\ln 2 \Delta z_x}^2)$$

represents a Gaussian distribution with a mathematical expectation of 0 and a variance of $$\frac{\Delta z_k}{8\ln 2 \Delta z_x}^2.$$

Downsampling $D_k$: after the filtered x slice is obtained, it needs to be downsampled to obtain a low-resolution image $y_k$, and the downsampling factor is represented by $$\frac{\Delta z_k}{\Delta z_x}.$$

Since this factor is not necessarily an integer, the present application performs downsampling in the frequency domain, and ua low-pass filter is used to truncate all high-frequency components before downsampling in the frequency domain to avoid signal aliasing.

Noise $\varepsilon_k$: the Signal-to-noise Ratio (SNR) of the reconstructed high-resolution CT image x is calculated, and the noise in x is measured by a standard deviation of an image area and background. If SNR>3, the noise at this time is similar to a Gaussian distribution, and noise $\varepsilon_k$ complying with the same Gaussian distribution is added in the degradation process.

3) Since the output x of the generative network is limited by the processing result of the degradation network, the high-resolution image x of the generative network output is actually expressed as:

$$x = f_\theta(z), s.t. \ y_k = D_k H_k T_k x + \varepsilon_k \ k=1,2,\ldots,N;$$

4) Random noises v and z are combined and input into the network to enhance the robustness of $f_\theta$ learning and prevent local optimal solution. The random noise v obeys the Gaussian distribution, and each element is extracted from $v \sim N(0, \sigma^2)$ independently. The size of noise v is controlled by the parameter $\sigma$, and if Gaussian noise is not needed, then $\sigma=0$ By combining the Gaussian noise $\varepsilon_k$ in the low-resolution CT image obtained in the above steps, the learning formula of $f_\theta$ is:

$$\min_{x,\theta} l(x - f_\theta(z+v)) + \tau \sum_{K=1}^{N} \|o_k - D_k H_k T_k x - \varepsilon_k\|_2^2;$$

where $l(\bullet)$ represents a loss function; $\tau$ is the weight of the loss function of the degradation network in the total loss, $\tau>0$; $\|\bullet\|_2$ is a $l_2$ norm of $\bullet$, i.e., extracting the square root of the sum of squares of all vectors in a matrix, also known as an Euclid's norm.

5) In order to improve the clarity of high-resolution CT reconstructed images and preserve the details of image edges, a TV regularization term is added to the reconstructed x, and a $l_1$ norm is used for constraint. Therefore, $f_\theta$ can be realized by the following formula:

$$\min_{x,\theta} l(x - f_\theta(z+v)) + \tau \sum_{K=1}^{N} \|o_k - D_k H_k T_k x - \varepsilon_k\|_2^2 + \mu\|\nabla x\|_1;$$

$\mu$ is the weight parameter of the TV regularization term, and $\mu \geq 0$, and $\mu=0$ if the constraint of the TV regularization term is not needed; $\nabla x$ represents the image gradient in three orthogonal directions of x, and $\|\nabla x\|_1$ represents a $l_1$ norm of x, that is, the sum of the absolute values of each element in the calculation matrix, which is also called a sparse rule operator.

6) The present application adopts the iterative strategy of jointly optimizing (x, $\theta$) or the technology of alternating optimization between X and $\theta$ to solve the minimum problem of the above equation. Since the loss function $l(\bullet)$ is a Mean Squared Error(MSE) loss, $f_\theta$ can be used instead of x:

$$\min_{\theta} \sum_{K=1}^{N} \|o_k - D_k H_k T_k f_\theta(z+v) - \varepsilon_k\|_2^2 + \mu\|\nabla f_\theta(z+v)\|_1;$$

An Adam algorithm is used to optimize the network parameter $\theta$ and the minimum value of the above equation is obtained.

In the testing stage, the CT super-resolution reconstruction model only includes the image acquisition module, the preprocessing module and the generative network part in the super-resolution module, and the output of the generative network is taken as the reconstruction result x of the high-resolution CT image. If the input is o, the image after preprocessing module is the initial value z, z is the input of the generative network, and finally the output of the generative network is taken as the expected result, then the required high-resolution reconstructed CT image x is obtained from the following equation:

$$z = DHFo$$

$$x = f_\theta(z);$$

where D, H and F are the algorithm matrices in the TV-based super-resolution reconstruction algorithm, and $f_\theta$ is the nonlinear generation function in the generative network.

The present application only relies on the low-resolution CT data obtained from a specific patient, and allows the super-resolution reconstruction model to be customized for individual patients. Secondly, the input of the generative network in the present application is the data after the super-resolution reconstruction algorithm based on TV, and Gaussian noise is added to the input by adopting the strategy of "Noise2noise" instead of the original low-resolution CT image. "Noise2noise" refers to adding a noise v (Gaussian noise is used in this present application) with an average value of 0 to the image input into the generative network. At this time, the input becomes an image z+v with the noise v, z is an image reconstructed from o through super resolution, and o used for evaluation is the original image without the v noise. Under the condition that no noise image can be obtained as a label, the denoising method of "Noise2noise" is introduced in the present application, so that the quality of the reconstructed image can be improved, and the denoising effect can also be achieved under the condition that no noise or high-resolution CT image is used as a label. Secondly, the present application adds a degradation network to supervise the reconstruction result of the generative network, and compares the degenerated result of the generative network with the original image data, and the whole process does not need high-resolution data as a label. In addition, the process of filtering and down-sampling in degradation network is carried out in the frequency domain, which can solve the problem that the down-sampling factor is not an integer.

Patient-specific learning can be carried out on the CT super-resolution reconstruction network without a large number of paired training data sets, and only low-quality CT data are obtained for a certain patient, which takes less time, requires less radiation scanning dose and causes lower radiation damage to the patient; the present application supports the exclusive network training for specific patients, which can make up for the deficiency that the data-oriented training network cannot be applied to all patients, and has higher generalization.

In addition, the present application can also have the following alternatives:

1. The structure of the generative network used in the present application is similar to 3D U-Net. If the structure of the generative network is changed to other networks that can realize image reconstruction, the same inventive purpose can be achieved.

2. The data type used in the present application is CT data, aiming at super-resolution reconstruction of CT data to obtain high-resolution CT data. If the data is changed to other medical image data modes, such as MRI, ultrasound images, etc., it can also be subjected to super-resolution reconstructed to achieve the same inventive purpose;

3. The preprocessing module in the present application adopts a super-resolution reconstruction algorithm based on TV, aiming at obtaining a reconstructed image with higher resolution than the original image and using it as a network input for later training. Other reconstruction methods may also be used to obtain an image with improved resolution, and the same inventive purpose can be achieved.

4. The degradation network in the present application adopts the method of multiplying multiple matrices to simulate the situation that will affect the image quality in actual CT acquisition to obtain a low-resolution CT image, and the same inventive purpose can be achieved by replacing it with other down-sampling methods to obtain a low-resolution image from a high-resolution image.

Figure 4:
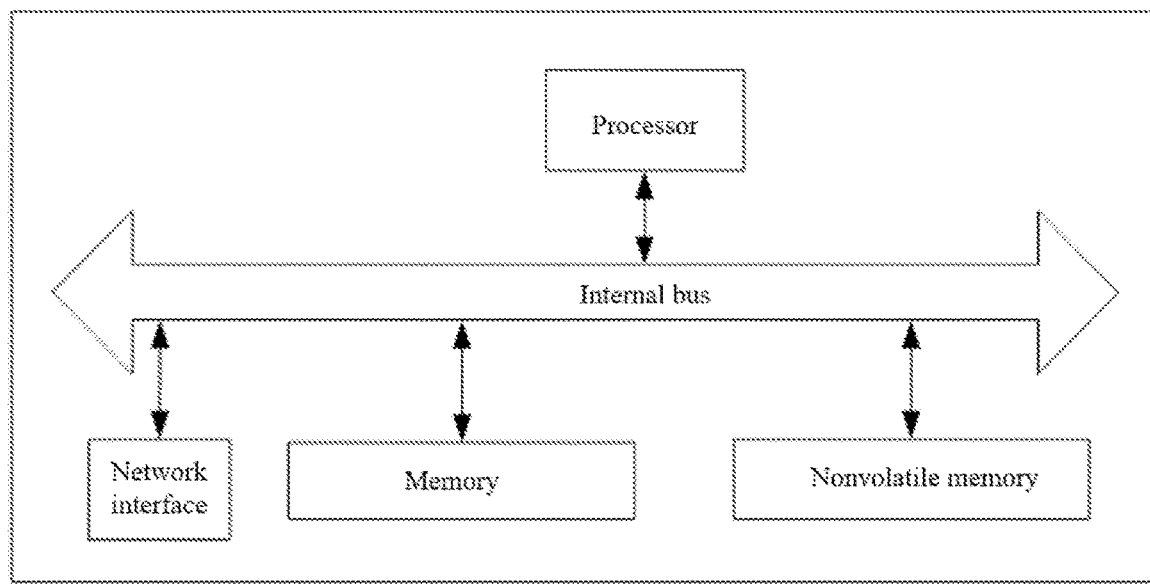
FIG. 4 is a schematic diagram of the device according to an embodiment of the present application.

Referring to FIG. 4, the embodiment of the present application also provides a label-free adaptive CT super-resolution reconstruction device based on a generative network, which further includes a memory and one or more processors. The memory stores executable codes, and when executing the executable codes, the one or more processors implements the label-free adaptive CT super-resolution reconstruction method based on the generative network in the above embodiment.

An embodiment of a label-free adaptive CT super-resolution reconstruction device based on a generative network of the present application can be applied to any device with data processing capability, which can be a device or apparatus such as a computer. The embodiment of the device can be realized by software, or by hardware or a combination of hardware and software. Taking software implementation as an example, as a logical device, it is formed by reading the corresponding computer program instructions in the nonvolatile memory into the memory through the processor of any equipment with data processing capability. From the hardware level, as shown in FIG. 4, it is a hardware structure diagram of any equipment with data processing capability where the label-free adaptive CT super-resolution reconstruction device based on the generative network of the present application is located. In addition to the processor, memory, network interface and nonvolatile memory shown in FIG. 4, any equipment with data processing capability where the device is located in the embodiment usually includes other hardware according to the actual functions of the equipment with data processing capability, which will not be described here again. The realization process of the functions and actions of each unit in the above-mentioned device is detailed in the realization process of the corresponding steps in the above-mentioned method, and will not be repeated here.

For the device embodiment, since it basically corresponds to the method embodiment, it is only necessary to refer to part of the description of the method embodiment for the relevant content. The device embodiments described above are only schematic, in which the units described as separate components may or may not be physically separated, and the components displayed as units may or may not be physical units, that is, they may be located in one place or distributed to multiple network units. Some or all of the modules can be selected according to actual needs to achieve the purpose of the solution of the present application. Those skilled in the art can understand and implement it without creative labor.

An embodiment of the present application further provides a computer-readable storage medium, on which a program is stored; when executed by a processor, the program implements the label-free adaptive CT super-resolution reconstruction method based on a generative network in the above embodiment.

The computer-readable storage medium can be an internal storage unit of any device with data processing capability as described in any of the previous embodiments, such as a hard disk or a memory. The computer-readable storage medium can also be an external storage device of any device with data processing capability, such as a plug-in hard disk, Smart Media Card (SMC), SD card, Flash Card and the like provided on the device. Further, the computer-readable storage medium can also include both internal storage units and external storage devices of any device with data processing capability. The computer-readable storage medium is used for storing the computer program and other programs and data required by any equipment with data processing capability, and can also be used for temporarily storing data that has been output or will be output.

The above is only the preferred embodiment of the present application, and it is not intended to limit the present application. Any modification, equivalent substitution or improvement made within the spirit and principle of the present application shall be included in the protection scope of the present application.

What is claimed is:

1. A label-free adaptive CT super-resolution reconstruction method based on a generative network, comprising steps of:
   step S1, acquiring original CT image data, preprocessing the original CT image data by a super-resolution reconstruction algorithm based on total variation to obtain an image to be reconstructed, and combining the image with random noise and inputting combined data into the generative network to enhance the robustness of the generative network;
   wherein the step of obtaining the image to be reconstructed in step S1 comprises sub-steps of:
   step S1.1, obtaining an initial high-resolution CT image from an original low-resolution CT image by a super-resolution reconstruction algorithm based on total variation, wherein the super-resolution reconstruction algorithm based on total variation comprises a geometric transformation matrix, a motion blur matrix and a sampling matrix;
   step S1.2, obtaining gradient transformation of each CT slice in x and y directions according to the initial high-resolution CT image and pixel coordinates thereof;

step S1.3, obtaining the total variation regularization term of the initial high-resolution CT image according to the gradient transformation of the initial high-resolution CT image in x and y directions; and step S1.4, adding the total variation regularization term to the loss function of the super-resolution reconstruction algorithm based on total variation, continuously optimizing the loss function by a gradient descent method to obtain a minimum value thereof, and obtaining the image to be input into the generative network for reconstruction;

wherein in step S1, the random noise v obeys Gaussian distribution, each element is independently extracted from $v \sim N(0, \sigma^2)$; a size of the noise is controlled by a parameter $\sigma$; if Gaussian noise is not needed, $\sigma=0$;

and wherein a process of step S1.1 to step S1.4 comprises sub-steps of:

step S101, performing CT scanning on a target part of a patient to obtain original data o, wherein the original data o is a low-resolution CT image;

step S102, reconstructing, by a TV-based super-resolution reconstruction algorithm the low-resolution CT image to get an initial value z, and inputting the initial value z into the generative network as an image to be reconstructed, wherein an equation for obtaining the initial value z is:

$$\min \|z\|_{v} \text{ s.t. } o = DHFz$$

$$\|z\|_{TV} = \|D_1 z\|_1 + \|D_2 z\|_1$$

$$D_1 = \sum_{i,j} |z_{i,j} - z_{i-1,j}| * z$$

$$D_2 = \sum_{i,j} |z_{i,j} - z_{i,j-1}| * z$$

where i and j represent the pixel coordinates in the initial value z, $\|z\|_{TV}$ represents a TV regularization term of z, $D_1$ represents the gradient transformation in z direction, $D_2$ represents the gradient transformation in y direction, and $\|\cdot\|_1$ is a norm of $l_1$; o=DHFz is an imaging model of the TV-based super-resolution reconstruction algorithm, and F is the geometric transformation matrix; H is a motion blur matrix; D is the sampling matrix, o is the low-resolution CT image, and z is the initial high-resolution CT image to be obtained; a gradient descent method is used to optimize the algorithm, and a solution objective is shown in the following formula:

$$\arg \min_{o} \left( \|z\|_{TV} + \frac{1}{2} \|DHFz - o\|_2^2 \right)$$

where $\|\cdot\|_2$ is a norm of $l_2$;

step S2, the generative network reconstructing the preprocessed image by using a nonlinear generation function to obtain a high-resolution CT image, and inputting the high-resolution CT image into a degradation network;

step S3, the degradation network processing the high-resolution CT image by rigid body transformation matrices, slice coding matrices and down-sampling matrices, and adding Gaussian noise to obtain a low-resolution CT image; and step S4, the generative network and the degradation network jointly affecting a loss function, updating parameters of the generative network in a back propagation, while keeping the degradation network unchanged, which mainly comprises the following steps: comparing the low-resolution CT image obtained by the degradation network with the original data, and adding the low-resolution CT image into the loss function of the generative network by using a Euclidean norm as a constraint; calculating a total variation regularization term for the reconstructed high-resolution CT image; adding the total variation regularization term to the loss function by using a sparse rule operator as a constraint to improve the clarity of the high-resolution CT image and preserving details of edges of the image; calculating a gradient of loss function by using an Adam algorithm, and realizing update of the parameters of the generative network.

2. The label-free adaptive CT super-resolution reconstruction method based on a generative network according to claim 1, wherein in step S2, the generative network is pre-trained on CT data of a same target area in advance, so as to speed up a convergence speed when fine-tuning parameters for specific patients, and to improve the reconstruction effect; N low-resolution original CT image data of individual patients are obtained and used to train the generative network to realize CT super-resolution reconstruction, which can realize a customized CT super-resolution reconstruction system for individual patients.

3. The label-free adaptive CT super-resolution reconstruction method based on a generative network according to claim 1, wherein in step S3, a value of a $k^{th}$ rigid body transformation matrix is calculated by aligning a $k^{th}$ low-resolution original CT image with a first original CT image.

4. The label-free adaptive CT super-resolution reconstruction method based on a generative network according to claim 1, wherein in step S3, a slice thickness $\Delta z_x$ of the reconstructed high-resolution CT image is smaller than a slice thickness $\Delta z_k$ of the obtained low-resolution CT image; when low-resolution CT images are obtained from a high-resolution CT image by the degradation network, each low-resolution CT image is operated corresponding to a plurality of CT slices of the high-resolution CT image; slice distribution of the high-resolution CT image in the z direction is selected by introducing a slice coding matrix, a Gaussian distribution with a wide base and a narrow central peak is selected to represent the slice coding matrix, and a full width at half maximum of the slice coding matrix is a $\Delta z_k / \Delta z_x$ voxel in z direction.

5. The label-free adaptive CT super-resolution reconstruction method based on a generative network according to claim 1, wherein in step S3, the down-sampling operation is performed in a frequency domain, and all high-frequency components are truncated by a low-pass filter before down-sampling in the frequency domain to avoid signal aliasing.

6. The label-free adaptive CT super-resolution reconstruction method based on a generative network according to claim 1, wherein in step S3, a signal-to-noise ratio of the reconstructed high-resolution CT image is calculated, and the noise in the high-resolution CT image is measured by a standard deviation between an image area and background; if the signal-to-noise ratio is greater than 3, the noise at this time is similar to a Gaussian distribution, and in a degradation process, noise complying with a same Gaussian distribution is added; if the signal-to-noise ratio is less than or equal to 3, no additional noise is added.

7. The label-free adaptive CT super-resolution reconstruction method based on a generative network according to claim 1, wherein in step S4, the total variation regularization term is added to the reconstructed high-resolution CT image, image gradients in three orthogonal directions of the reconstructed high-resolution CT image are calculated and constrained by sparse rule operators, and weight parameters are added to the total variation regularization term to be added to the loss function and used to train and update the parameters of a nonlinear generation function in the generative network together with a loss part of the degradation network in the loss function.

8. The label-free adaptive CT super-resolution reconstruction method based on a generative network according to claim 1, wherein in step S4, an iterative strategy of jointly optimizing the high-resolution CT image x reconstructed by the generative network and a parameter θ in the nonlinear generation function or a technique of alternately optimizing the high-resolution CT image x and the parameter θ in the nonlinear generation function is adopted to solve the problem of calculating a minimum value of the loss function.

9. A label-free adaptive CT super-resolution reconstruction device based on a generative network, comprising a memory and one or more processors, wherein executable codes are stored in the memory, and when executing the executable codes, the one or more processors implements the label-free adaptive CT super-resolution reconstruction method based on a generative network according to claim 1.

10. A label-free adaptive CT super-resolution reconstruction system based on a generative network, comprising:
an acquisition module configured for acquiring low-resolution original CT image data;
a preprocessing module configured for performing super-resolution reconstruction on original CT images based on total variation to obtain an initial value; and
a super-resolution reconstruction for performing high-resolution reconstruction on the initial value, wherein the module comprises a generative network based on deep learning and a degradation network for fitting low-resolution images from high-resolution images; the generative network and the degradation network jointly affect a loss function, and update parameters of the generative network in a back propagation while the degradation network remains unchanged;
wherein the preprocessing module is further configured for performing following steps:
step S1.1, obtaining an initial high-resolution CT image from an original low-resolution CT image by a super-resolution reconstruction algorithm based on total variation, wherein the super-resolution reconstruction algorithm based on total variation comprises a geometric transformation matrix, a motion blur matrix and a sampling matrix;
step S1.2, obtaining gradient transformation of each CT slice in x and y directions according to the initial high-resolution CT image and pixel coordinates thereof;
step S1.3, obtaining the total variation regularization term of the initial high-resolution CT image according to the gradient transformation of the initial high-resolution CT image in x and y directions; and
step S1.4, adding the total variation regularization term to the loss function of the super-resolution reconstruction algorithm based on total variation, continuously optimizing the loss function by a gradient descent method to obtain a minimum value thereof, and obtaining the image to be input into the generative network for reconstruction;
wherein the random noise ν obeys Gaussian distribution, each element is independently extracted from ν~N(0, $\sigma^2$); a size of the noise is controlled by a parameter σ; if Gaussian noise is not needed, σ=0;
and wherein a process of step S1.1 to step S1.4 comprises sub-steps of:
step S101, performing CT scanning on a target part of a patient to obtain original data o, wherein the original data o is a low-resolution CT image;
step S102, reconstructing, by a TV-based super-resolution reconstruction algorithm the low-resolution CT image to get an initial value z, and inputting the initial value z into the generative network as an image to be reconstructed, wherein an equation for obtaining the initial value z is:

$$\min \|z\|_{zv} \ \text{s.t.} \ o = DHFz$$

$$\|z\|_{TV} = \|D_1 z\|_1 + \|D_2 z\|_1$$

$$D_1 = \sum_{i,j} |z_{i,j} - z_{i-1,j}| * z$$

$$D_2 = \sum_{i,j} |z_{i,j} - z_{i,j-1}| * z$$

where i and j represent the pixel coordinates in the initial value z, $\|z\|_{TV}$ represents a TV regularization term of z, $D_1$ represents the gradient transformation in z direction, $D_2$ represents the gradient transformation in y direction, and $\|\cdot\|_1$ is a norm of $l_1$; o=DHFz is an imaging model of the TV-based super-resolution reconstruction algorithm, and F is the geometric transformation matrix; H is a motion blur matrix; D is the sampling matrix, o is the low-resolution CT image, and z is the initial high-resolution CT image to be obtained; a gradient descent method is used to optimize the algorithm, and a solution objective is shown in the following formula:

$$\arg \min_o \left( \|z\|_{TV} + \frac{1}{2} \|DHFz - o\|_2^2 \right)$$

where $\|\cdot\|_2$ is a norm of $l_2$.

* * * * *